United States Patent [19]

McCoy

[11] Patent Number: 4,764,172
[45] Date of Patent: Aug. 16, 1988

[54] ARTICULATED ANKLE

[76] Inventor: Allen J. McCoy, 18790 McCoy Rd., Livingston, La.

[21] Appl. No.: 935,714

[22] Filed: Nov. 28, 1986

[51] Int. Cl.[4] ............................................. A61F 2/66
[52] U.S. Cl. ......................................... 623/49; 623/52
[58] Field of Search .................................... 623/47–53

[56] References Cited

U.S. PATENT DOCUMENTS

| 2,289,154 | 7/1942 | Van Cise | 623/49 |
| 2,470,480 | 5/1949 | Fogg | 623/47 |
| 3,196,463 | 7/1965 | Farneth | 623/49 |
| 4,442,554 | 4/1984 | Copes | 623/47 |

OTHER PUBLICATIONS

Brochure–Copes/Bionic Ankle by Copes, Inc.

Primary Examiner—Richard J. Apley
Assistant Examiner—James Prizant
Attorney, Agent, or Firm—Fleit, Jacobson, Cohn & Price

[57] ABSTRACT

Herein disclosed is an articulated ankle joint for use in an artificial limb to connect a foot prosthesis to a leg prosthesis. The joint has foot and leg plates for attachment to the respective prostheses, a stem assembly which includes a coil spring and spherical bearing attached between the plates over a heel portion of the foot prosthesis, and a resistance assembly including a coil spring connected between the plates forwardly of the stem assembly. The joint can be used for performing a variety of physical activities in a natural and comfortable manner and has a natural appearance when clothed.

4 Claims, 2 Drawing Sheets

ARTICULATED ANKLE

BACKGROUND OF THE INVENTION

This invention relates to an articulated ankle assembly for use as an ankle joint between foot and leg prosthesia in an artificial limb.

Considerable research and development has been directed toward the provision of satisfactory artificial foot and leg prosthesis which would enable an amputee to walk and perform other physical functions with comfort and in the most natural manner possible. A significant area for development is the ankle joint which is critical in an artificial limb for obtaining natural, comfortable and indeed workable walking and other movements. Examples of earlier proposals relating to artificial joint structures may be seen in the following U.S. Pat. Nos.:

288,239—Nov. 13, 1883
1,213,114—Jan. 16, 1917
1,215,268—Feb. 6, 1917
2,617,115—Nov. 11, 1952
2,699,554—Jan. 18, 1955
3,196,463—July 27, 1965
4,442,554—Apr. 17, 1984

While at least certain of the earlier proposals may have found practical usage, there is a continuing demand to improve upon known designs particularly in the areas of user comfort, adaptability to users of different sex, age, weight and body type, and effectiveness in simulating the functioning of a natural ankle joint.

SUMMARY OF THE INVENTION

The invention provides an artificial articulated ankle assembly for the general purpose indicated and which, it is believed, can be adapted to persons of different body weight, size and the like, can effectively accommodate a wide range of physical activities, and which has a substantially natural appearance when covered by clothing. Applicant, himself an amputee, has, for example, successfully employed a prosthesis incorporating an ankle joint in accordance with the invention for running, dancing, pivoting on one leg, and climbing. It is applicant's belief that the ankle joint may be useful in performing substantially any activity performed by a nonamputee.

Essentially, an ankle joint in accordance with the invention includes a foot plate for attachment to a foot prosthesis, a leg plate for attachment to a leg prosthesis, a stem assembly connected between the plates over a heel-simulating portion of the foot prosthesis, the stem assembly including a spherical bearing for providing swivelling movements of the foot prosthesis on the leg prosthesis, a first coil spring encircling the stem assembly for reacting between the plates and providing a degree of resistance to said swivelling movements, and a resistance assembly including a second coil spring connected between the plates forwardly of the stem assembly.

The stem assembly may preferably include threaded length adjustment means whereby the spring resistance and general operating characteristics of the joint may be varied to suit user needs. The respective spring may, for example, comprise or have the characteristics of automotive valve springs.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
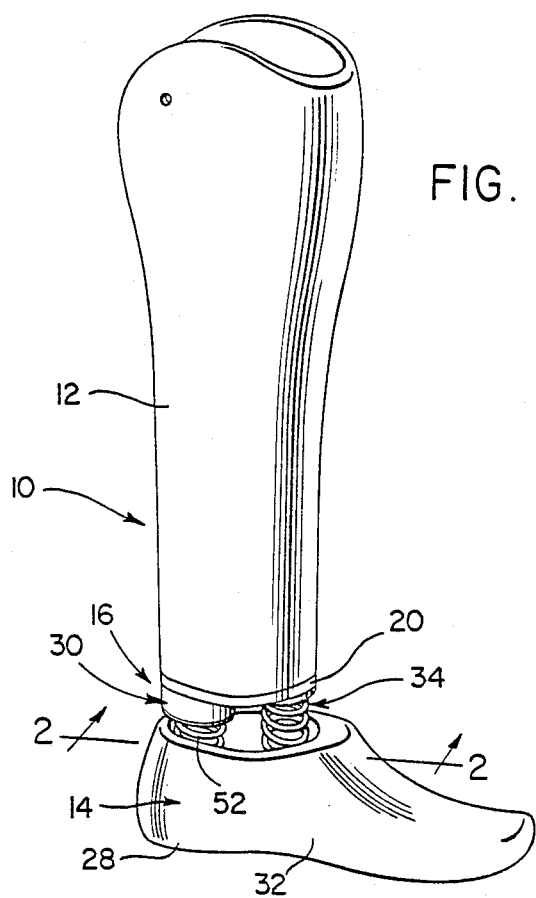
FIG. 1 is a perspective view of an artificial limb which includes an articulated ankle in accordance with the invention.
Figure 6:
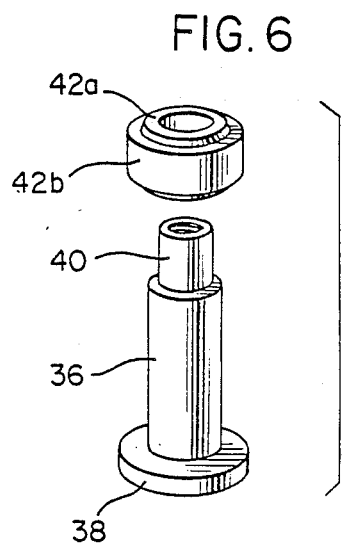
FIG. 6 is an exploded perspective view of parts of the ankle.
Figure 2:
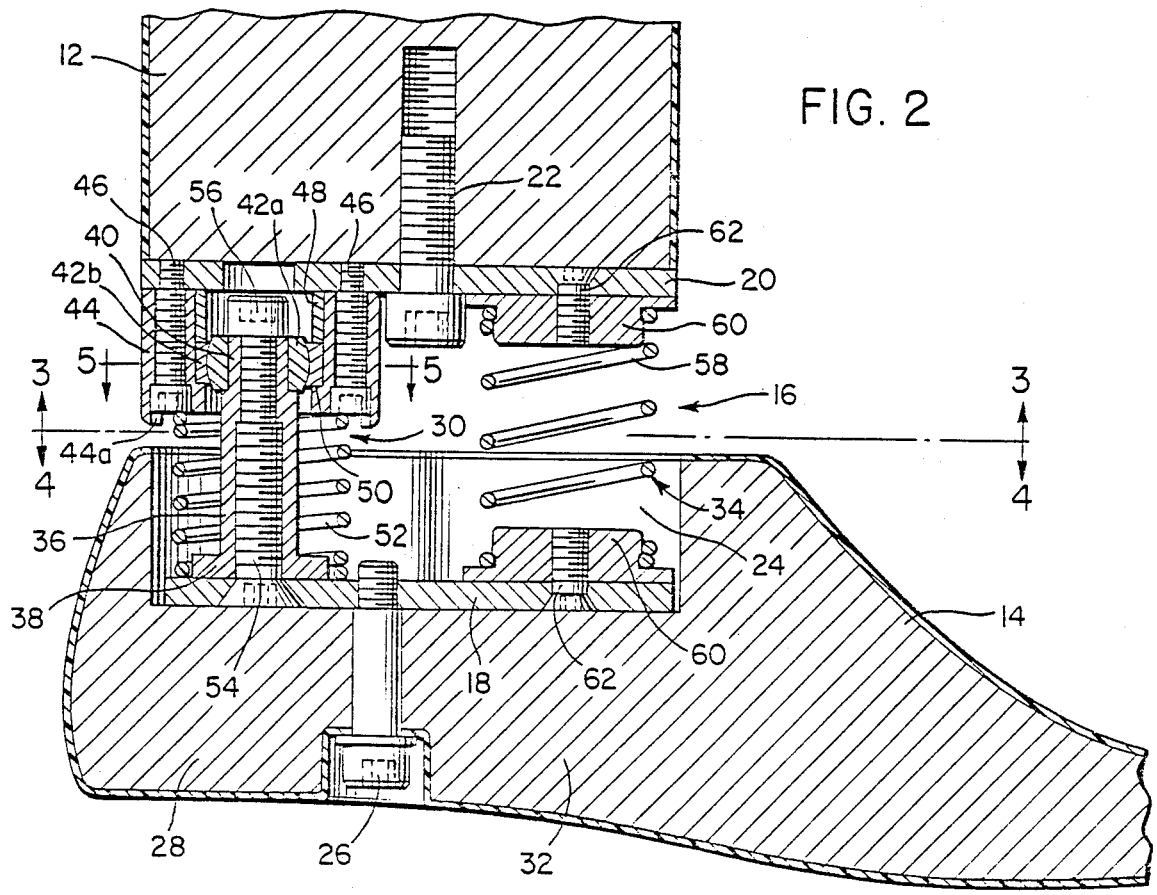
FIG. 2 is an enlarged sectional view on line 2—2 of FIG. 1.

An artificial limb 10 (FIG. 1) includes a leg prosthesis 12, a foot prosthesis 14, for example a Kingsley Simes foot, and an artificial ankle assembly 16 in accordance with the invention connecting the foot prosthesis to the leg prosthesis.

Figure 3:
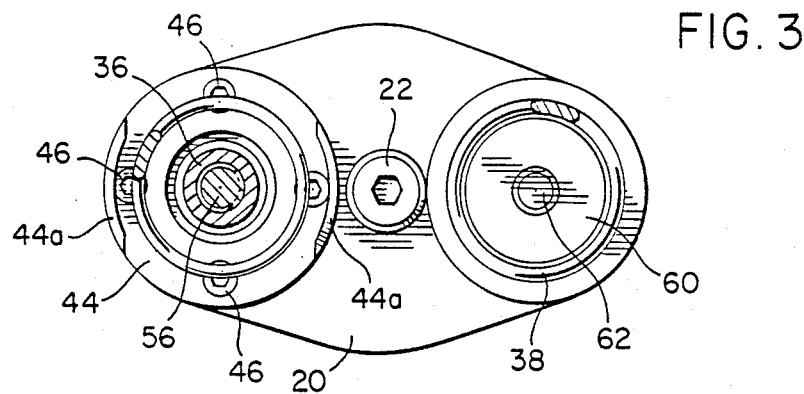
FIG. 3 is a sectional view on line 3—3 of FIG. 2.
Figure 4:
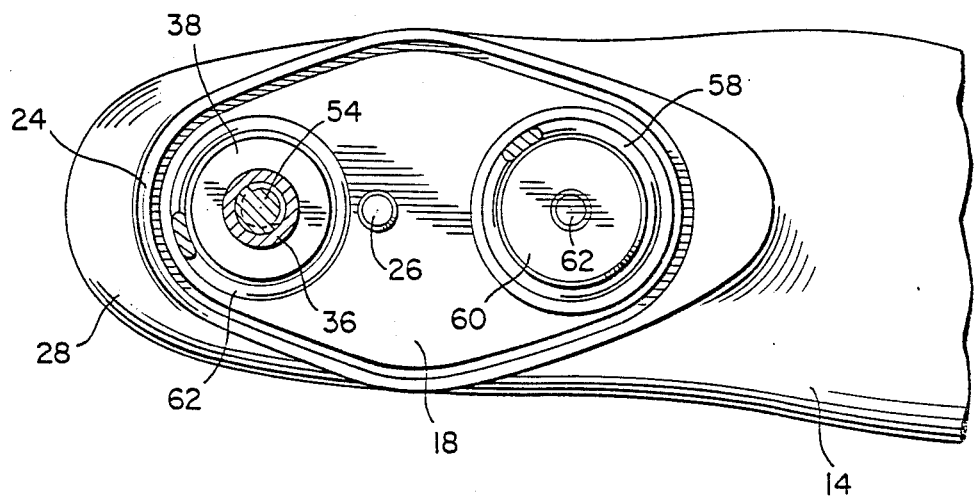
FIG. 4 is a sectional view on line 4—4 of FIG. 2.
Figure 5:
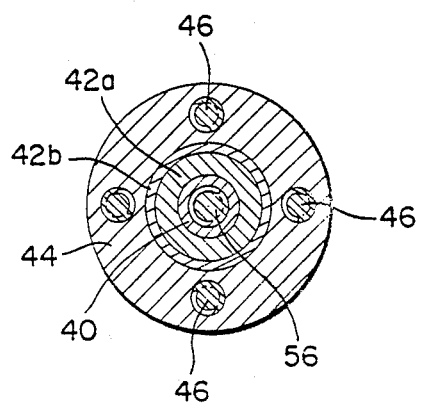
FIG. 5 is a sectional view on line 5—5 of FIG. 2.

Referring in more detail to FIGS. 2-6, ankle assembly 16 includes a foot plate 18 and a leg plate 20, each of which may be of generally diamond-shape form, with rounded corners as shown in FIGS. 3 and 4. Leg plate 20 is secured to the base of prosthesis 12 by a centralized hexagon socket-head cap screw 22, and foot plate 18 is secured in a well 24 in prosthesis 14 by a further hexagon socket head cap screw 26. Well 24 is formed generally over the heel and arch-simulating areas of prosthesis 14. Connected between plates 18 and 20 over the heel-simulating portion 28 of prosthesis 14, is a stem assembly 30 described in more detail below, and connected between the plates forwardly of the stem assembly, generally over arch-simulating portion 32 of prosthesis 14, is a resistance assembly 34, also described in more detail below.

The stem assembly 30 comprises a tubular internally threaded support rod 36 with a base flange 38 on plate 18, and a reduced-diameter upper end 40 which receives inner race 42a of a spherical bearing having an outer race 42b retained in a bearing housing 44. The spherical bearing is of a type allowing swivelling movement of the races relative to the axis of rod 36 and also rotation about the axis so as to allow up and down swivelling movement and rotation of the joint. The bearing may, for example, be a Heim-LHSSVV-S6 Alinabal spherical bearing. Bearirg housing 44 is secured to plate 20 by screw fasteners 46 and a spacer 48, preferably in the form of a spring, retains outer bearing race 42b in position against a housing shoulder 50. A first coil spring 52 encircles rod 36 and is laterally located by flange 38 and lips 44a at the base of housing 44. The spring acts between plate 18 and bearing housing 44 to provide resistance to swivelling of the spherical bearing. Rod 36 is secured to plate 18 by a screw 54 and a second screw 56 is threaded into the top of rod 36. The provision of the screws allows the effective length of rod 36 to be adjusted thereby varying the "stiffness" of the joint and its resistance to swivelling.

Resistance assembly 34 also resists swivelling and rotation of the joint about the axis of rod 36 and comprises a second coil spring 58 located by end caps 60 attached by screws 62 to the respective plates 18 and 20.

Coil springs 52 and 58 may comprise automative valve springs.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An articulated ankle joint comprising a foot plate for attachment to a foot prosthesis, a leg plate for attachment to a leg prosthesis, a stem assembly connected between the plates for location over a heel portion of the foot prosthesis, the stem assembly including a spherical bearing for providing relative up and down and swivelling movements of the plates and relative rotational movements of the plates about an axis of the stem assembly, a first coil spring encircling the stem assembly, at least in part, for reacting between the plates and providing a degree of resistance to said swivelling movements, and a resistance assembly including a second coil spring connected between the plates forwardly of the stem assembly for providing resistance to both said swivelling and rotational movements of the plates.

2. A joint as defined in claim 1 wherein the stem assembly includes a bearing support rod having one end connected to one of said plates and another end forming a seat for an inner race of the spherical bearing, the stem assembly further including a bearing housing attached to the other of said plates and retaining an outer race of the spherical bearing, and wherein the first coil spring is located around said rod between said one of the plates and the bearing housing.

3. An articulated ankle joint between a leg prosthesis and a foot prosthesis to enable relative movement which closely simulates a natural ankle joint, said ankle joint comprising a rigid stem extending upwardly from the foot prosthesis, a spherical bearing assembly mounted on the upper end of the stem, a bearing housing mounted on the leg prosthesis and engaging the spherical bearing assembly in a manner to retain the foot prosthesis and leg prosthesis in assembled relation and to enable relative movement between the leg prosthesis and foot prosthesis, a coil spring encircling the stem in concentric spaced relation thereto and biasing the foot prosthesis and leg prosthesis apart and resisting relative movement therebetween, a second coil spring resiliently interconnecting the leg prosthesis and foot prosthesis in forwardly spaced relation to the coil spring encircling the stem to further resist relative movement between the leg prosthesis and foot prosthesis, said spherical bearing assembly and bearing housing including coacting means enabling relative movement between the leg prosthesis and foot prosthesis about a generally vertical axis generally in alignment with the heel portion of the foot prosthesis, universal pivotal movement, inversion, eversion, fore and aft rocking, swivelling and vertical movement cushioning with all relative movement being resisted and controlled by said coil springs, said coil springs being interchangeable with other coil springs having different resilient characteristics to enable the ankle joint to be adapted for use with individuals having different physical characteristics.

4. The ankle joint as defined in claim 3 wherein said spherical bearing assembly includes an inner race, said stem including an upwardly facing shoulder engaging and receiving the inner race, fastener means securing the inner race to the stem, said bearing housing including a generally cylindrical structure having an inturned flange underlying and engaging the outer race of the spherical bearing assembly and a resilient spacer engaging the upper edge of the outer race with the inner and outer races of the spherical bearing assembly including partial spherical surfaces to enable universal movement between the stem and bearing housing with the coil spring and resilient spacer resisting such movement and cushioning such movement with both coil springs being free to move without restriction except for their end engaging the leg prosthesis and foot prosthesis, said spherical bearing assembly being located above the upper end of the coil spring which engages the lower end of the bearing housing.

* * * * *